United States Patent
Dale et al.

(10) Patent No.: US 11,433,247 B2
(45) Date of Patent: Sep. 6, 2022

(54) LEADLESS PACEMAKER WITH COLLAPSIBLE ANCHORING DEVICE

(71) Applicant: ST. JUDE MEDICAL, CARDIOLOGY DIVISION, INC., St. Paul, MN (US)

(72) Inventors: Theodore Dale, Corcoran, MN (US); Daniel Coyle, St. Louis Park, MN (US); Paul A. Belk, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 448 days.

(21) Appl. No.: 16/347,150

(22) PCT Filed: Nov. 2, 2017

(86) PCT No.: PCT/US2017/059725
§ 371 (c)(1),
(2) Date: May 2, 2019

(87) PCT Pub. No.: WO2018/085545
PCT Pub. Date: May 11, 2018

(65) Prior Publication Data
US 2020/0054882 A1 Feb. 20, 2020

Related U.S. Application Data

(60) Provisional application No. 62/416,874, filed on Nov. 3, 2016.

(51) Int. Cl.
*A61N 1/375* (2006.01)
*A61N 1/05* (2006.01)
*A61N 1/372* (2006.01)

(52) U.S. Cl.
CPC ......... *A61N 1/37518* (2017.08); *A61N 1/059* (2013.01); *A61N 1/3756* (2013.01); *A61N 1/37205* (2013.01); *A61N 1/37512* (2017.08)

(58) Field of Classification Search
CPC ............ A61N 1/37518; A61N 1/37512; A61N 1/059; A61N 1/37205; A61N 1/3756;
(Continued)

(56) References Cited

U.S. PATENT DOCUMENTS

| | | | |
|---|---|---|---|
| RE30,366 E * | 8/1980 | Rasor ................... | A61N 1/0573 607/35 |
| 7,389,134 B1 * | 6/2008 | Karicherla ........... | A61B 5/0215 600/375 |

(Continued)

FOREIGN PATENT DOCUMENTS

EP    2769750 A1    8/2014

OTHER PUBLICATIONS

International Search Report and Written Opinion for International Application No. PCT/US2017/059725, dated Apr. 3, 2018, 12 pages.

*Primary Examiner* — Mark W. Bockelman
(74) *Attorney, Agent, or Firm* — Armstrong Teasdale LLP

(57) ABSTRACT

The present disclosure provides improved leadless pacemakers. In one embodiment, the leadless pacemaker includes an implantable pulse generator releasably coupled to a collapsible anchoring device. The collapsible anchoring device includes at least one pacing electrode configured to contact tissue at a target site.

18 Claims, 8 Drawing Sheets

(58) Field of Classification Search
CPC .......... A61B 2017/00592; A61B 2017/00575; A61B 17/12122; A61B 17/12172; A61B 2017/12054; A61B 2017/00606; A61B 2017/00579; A61B 17/0057

See application file for complete search history.

(56) References Cited

U.S. PATENT DOCUMENTS

| | | | |
|---|---|---|---|
| 10,780,280 B2 * | 9/2020 | Friedman | A61N 1/37518 |
| 2006/0122522 A1 | 6/2006 | Chavan et al. | |
| 2012/0172690 A1 | 7/2012 | Anderson et al. | |
| 2013/0178908 A1 | 7/2013 | Huber | |
| 2016/0250474 A1 | 9/2016 | Stack et al. | |

\* cited by examiner

LEADLESS PACEMAKER WITH COLLAPSIBLE ANCHORING DEVICE

CROSS-REFERENCE TO RELATED APPLICATION

This application is the national stage entry of PCT/US2017/059725, filed on Nov. 2, 2017, which claims the benefit of priority to U.S. Provisional Patent Application No. 62/416,874, filed Nov. 3, 2016, the entire contents and disclosure of which are hereby incorporated herein by reference in their entirety.

BACKGROUND OF THE DISCLOSURE

Field of the Disclosure

The present disclosure generally relates to a leadless pacemaker and methods of making and using the same. In particular, the present disclosure relates to a leadless pacemaker including a collapsible anchoring device comprising at least one pacing electrode and configured to be coupled to an implantable pulse generator.

BACKGROUND ART

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is typically performed by implanting subcutaneously or sub-muscularly a conventional cardiac pacemaker (utilizing a pulse generator and pacing leads) near a patient's pectoral region or by implanting a leadless cardiac pacemaker directly into the patient's heart. Cardiac pacemakers generally comprise an implantable pulse generator ("IPG") including a battery and related circuitry, and a tissue interface, which couples generated pulses to cardiac tissue and sensed cardiac activity back to the IPG. In a conventional pacemaker, the IPG is implanted in a surface tissue plane (often sub-cutaneous or sub-muscular) and the tissue interface with the pacemaker is implemented as a lead that attaches proximally to the IPG and distally to cardiac tissue.

In contrast to a conventional pacemaker, a "leadless" pacemaker utilizes an IPG that is implanted directly into the heart of the patient so that the tissue interface with the pacemaker is near to or even an integral component of the IPG. Such a configuration reduces the need to create and maintain a separate "pocket" into which the IPG is implanted and reduces the need for a long electrical connection (i.e., "lead") between the IPG and the tissue interface.

SUMMARY OF THE DISCLOSURE

The present disclosure is directed to a leadless pacemaker comprising an implantable pulse generator and a collapsible anchoring device configured to be coupled to the implantable pulse generator. The collapsible anchoring device comprises at least one pacing electrode configured to contact tissue at a target site.

The present disclosure is further directed to an anchoring device for a leadless pacemaker. The anchoring device comprises a tubular member having a proximal end, a distal end, and an expanded configuration. The tubular member comprises an implantable pulse generator connector positioned on a proximal side thereof. The anchoring device further comprises an electrical connection that comprises at least one pacing electrode. The electrical connection extends from the implantable pulse generator connector to an outer surface of the tubular member such that at least one pacing electrode is configured to contact tissue at a target site.

The present disclosure is further directed to a method of delivering a leadless pacemaker to a target site. The method comprises providing an anchoring device comprising a tubular member having a proximal end, a distal end and an expanded configuration. The tubular member comprises an implantable pulse generator connector positioned on a proximal side thereof and an electrical connection extending from the implantable pulse generator to an outer surface of the tubular member such that the at least one pacing electrode is configured to contact tissue at a target site. The method further comprises advancing the anchoring device in a reduced configuration to the target site through a delivery device; deploying the anchoring device from the delivery device such that the anchoring device at least partially returns from the reduced configuration to an expanded configuration; and coupling an implantable pulse generator to the anchoring device via the implantable pulse generator connector.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Figure 1:
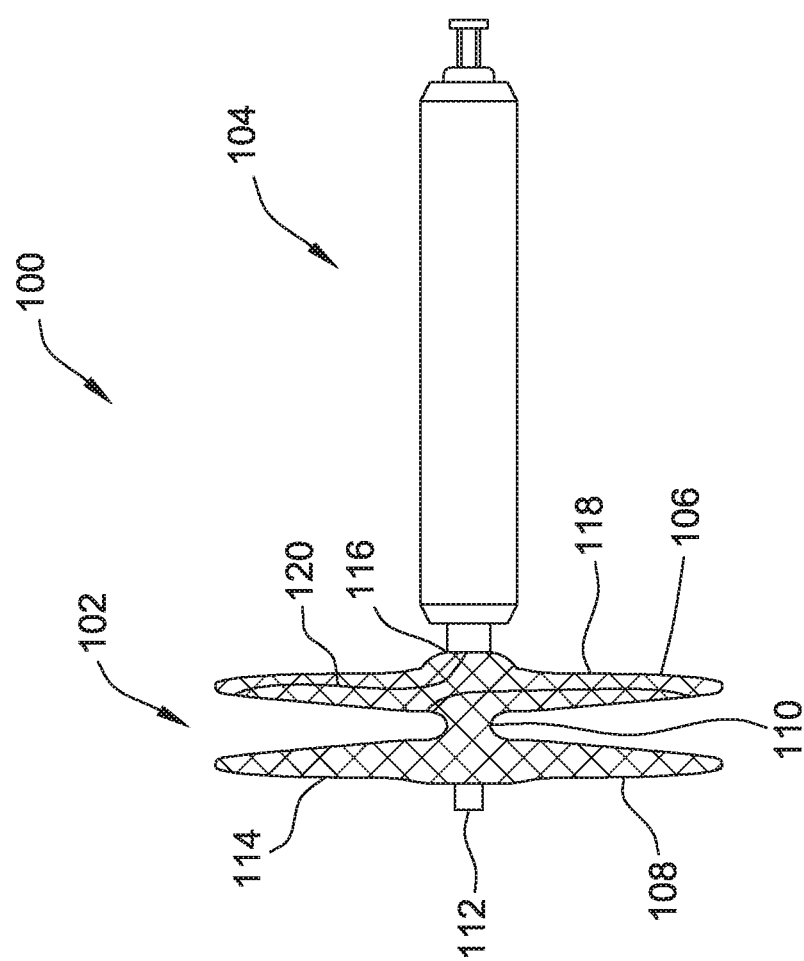
FIG. 1 shows a perspective view of one embodiment of a leadless pacemaker of the present disclosure including a collapsible anchoring device and an implantable pulse generator.

Unlike conventional pacemakers, leadless pacemakers are positioned and attached, or anchored, directly into the heart of a patient, such as in an atrial septal wall or into ventricular tissue. Because it may at times become desirable or necessary to remove the leadless pacemaker entirely from the patient's heart, to reposition a previously implanted leadless pacemaker to a different location within the patient's heart, or to replace a defective or inoperative implantable pulse generator of a previously implanted leadless pacemaker, it is generally desirable to provide a leadless pacemaker with an improved ability to be removed and/or repositioned within a patient's heart while reducing or minimizing the potential of tissue damage. It is further desirable to provide a leadless pacemaker including an implantable pulse generator ("IPG") that is more easily accessible, removable, and replaceable from an anchoring device of a leadless pacemaker, and thus from the patient's heart.

Thus, it is desirable to provide a leadless pacemaker configured to conform to the native tissue at a target site of the pacemaker and to reduce the potential of tissue damage that may occur upon repositioning or removing the leadless pacemaker, and in particular, upon repositioning or removing the anchoring device (or tissue interface) of the leadless pacemaker. It is also desirable to provide a leadless pacemaker comprising an IPG that is configured to be releasably coupled to an anchoring device to provide for improved ease of removal or replacement of the IPG. The present disclosure is directed to a leadless pacemaker comprising a collapsible anchoring device and an IPG either releasably or integrally coupled thereto. The collapsible anchoring device includes a tubular member having a proximal end, a distal end, and an IPG connector positioned on a proximal side thereof. An electrical connection comprising at least one pacing electrode extends from the IPG connector to an outer surface of the tubular member such that at least one pacing electrode is configured to contact tissue at the target site and provide the desired pacing.

The leadless pacemakers described herein include a collapsible anchoring device coupled to an IPG, either releasably or integrally, and are designed for delivery to a target site through a delivery catheter or the like. The anchoring device is formed of a flexible, tubular, mesh fabric, such as nitinol, and thus is capable of being constrained within the delivery catheter or the like during a minimally invasive delivery procedure and expanding to a predetermined configuration at the target site upon deployment for anchoring or positioning the anchoring device. Because the anchoring device is formed of a flexible, tubular mesh fabric, it is also possible to recapture the anchoring device in instances where removal and/or repositioning is desired. Further, by utilizing an anchoring device formed of a flexible, tubular mesh fabric, the anchoring device, and thus the leadless pacemaker, has an improved conformability to the native tissue at the target site, which in turn, improves the securement of the anchoring device, and thus the leadless pacemaker, to the target site. That is, by providing an anchoring device configured to conform to the native tissue of the target site, the anchoring device is more securely anchored, positioned, fixed, or attached to the target site. In addition, the configuration of the anchoring device also reduces the need for the leadless pacemaker to include more permanent anchoring or fixation mechanisms which may have an increased potential for tissue damage upon removal thereof.

For example, in one embodiment, the anchoring device is configured for placement through a septal wall, such as an atrial septal wall. In this embodiment, the anchoring device includes a tubular member having a disk-shaped proximal portion configured to be positioned on a proximal side of the septal wall, a disk-shaped distal portion configured to be positioned on a distal side of the septal wall, and a reduced diameter portion configured to extend between the proximal portion and the distal portion and through the opening or hole in the septal wall. In another embodiment, the anchoring device is configured for placement within the right or left ventricle. In one such embodiment, the anchoring device includes a tubular member having an expanded portion configured to frictionally engage the tissue at the target site. The expanded portion may be one of cylindrically-shaped, cone-shaped, strawberry-shaped, elliptically-shaped, or bulbous in an expanded configuration and may optionally comprise a disk-shaped portion positioned at a proximal end of the anchoring device. A plurality of hooks may be provided on the tubular member so as to attach or anchor the tubular member to the ventricular wall. In both embodiments, an anchoring device is provided that sufficiently attaches, anchors, fixes, or positions the leadless pacemaker to the target site while conforming to the native tissue, and thus, minimizing damage to surrounding tissue.

The anchoring device of the present disclosure may also comprise an IPG connector positioned on a proximal side thereof that is configured to releasably couple the anchoring device to an IPG, thus enabling an inoperative IPG (e.g., an IPG comprising a defective battery or a "dead" battery (i.e., a battery with an expired life)) to either be completely removed from a patient or replaced with a new IPG without the need for removal of the entire leadless pacemaker. Further, because the anchoring device is formed of a mesh fabric, such as nitinol, tissue growth over and around the anchoring device is promoted as compared to other conventional leadless pacemaker anchoring or fixation devices. This allows the anchoring device to remain in the body even after the IPG is removed without posing a significant risk to the patient.

The proximal portion of the anchoring device includes an electrical connection that extends from the IPG connector (or the IPG itself in embodiments where the IPG and anchoring device are integrally formed) to at least one portion of an outer surface of the tubular member such that at least one pacing electrode positioned on or within the electrical connection is configured to contact tissue at the target site. The electrical connection comprises at least one pacing electrode, or contact point, and in many embodiments comprises a plurality of pacing electrodes. Each pacing electrode is configured to provide electrical stimulation to the targeted pacing site or location and may be individually selected by a user, thus allowing a user to provide pacing at various points at the target site without having to reposition the leadless pacemaker. That is, any combination of the pacing electrodes may be selectively energized for providing pacing at various points around the circumference of the proximal portion.

Further, because of the use of multiple individually selectable pacing electrodes or contact sites on the anchoring device, a user may be able to more easily identify a desired pacing location without having to reposition the anchoring device. That is, a user may selectively provide energy to each of the pacing electrodes (or any combination thereof) via the delivery catheter or the like and determine which pacing electrode(s) is desired for use at the target site prior to removal of the delivery catheter. Such a determination may also be made using an IPG coupled to the anchoring device after removal of the delivery catheter. Further, because the anchoring device is repositionable, a user may also recapture and reposition the anchoring device if it is determined that it is desirable to provide pacing at an alternative location within the heart.

Figure 2:
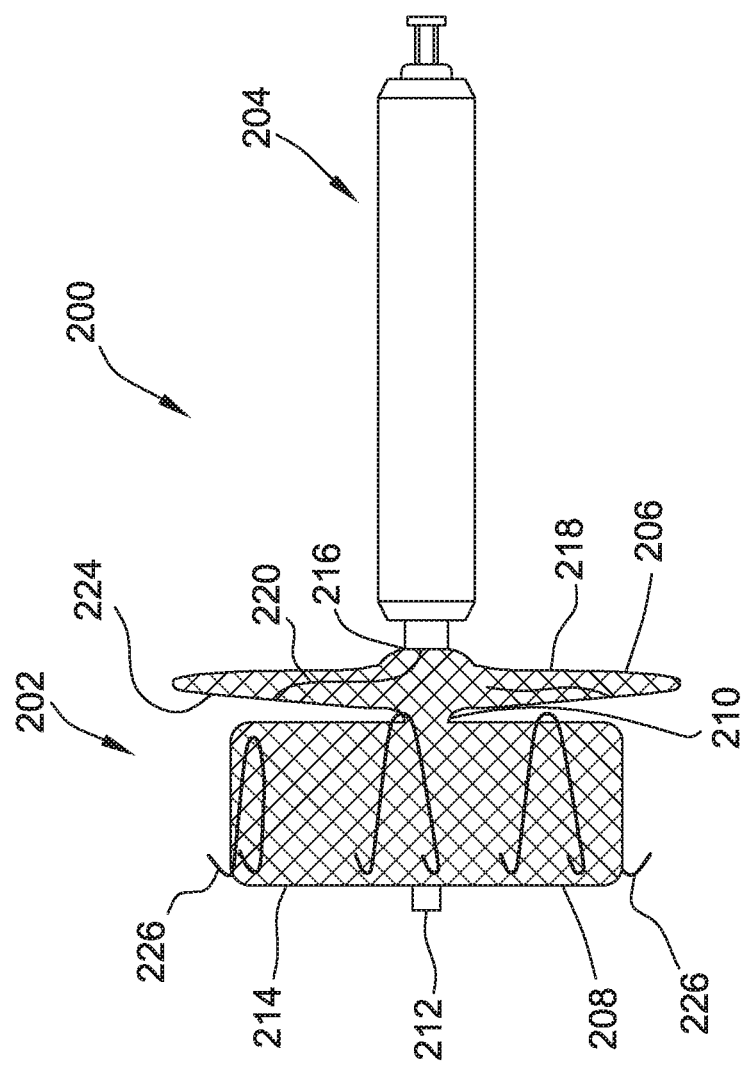
FIG. 2 shows a perspective view of another embodiment of a leadless pacemaker of the present disclosure including a collapsible anchoring device and an implantable pulse generator.
Figure 3:
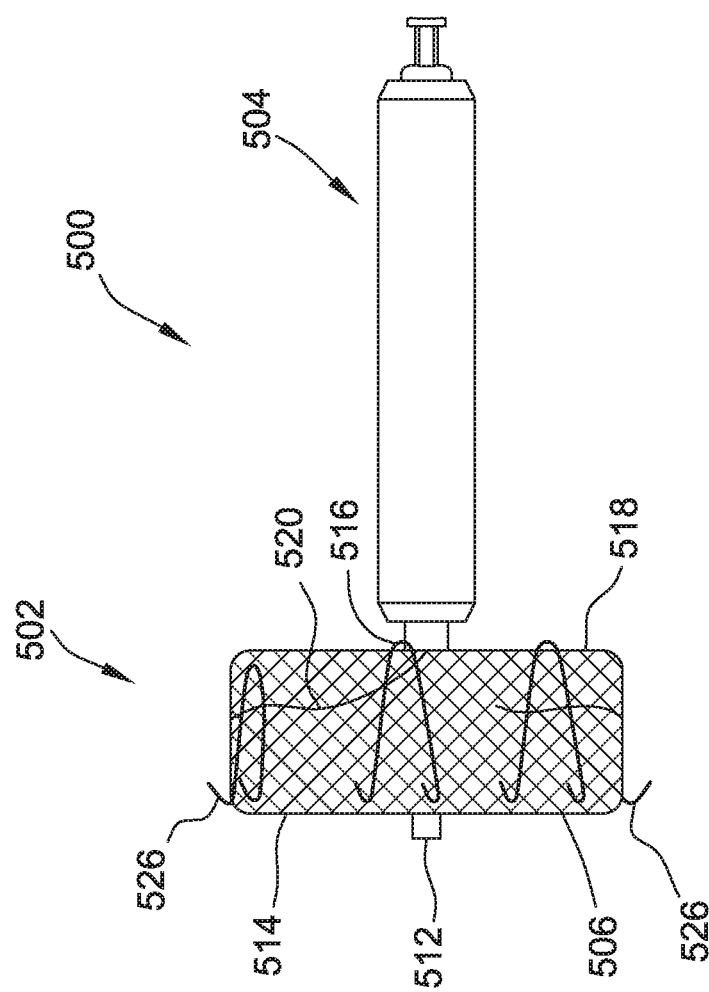
FIG. 3 shows a perspective view of another embodiment of a leadless pacemaker of the present disclosure including a collapsible anchoring device and an implantable pulse generator.

Turning to the Figures, FIGS. 1-3 illustrate three embodiments of a leadless pacemaker according the present disclosure, each including an anchoring device and an IPG.

Referring now to FIG. 1, there is shown a leadless pacemaker 100 in accordance with one embodiment of the present disclosure. Leadless pacemaker 100 includes an anchoring device 102 and an IPG 104 coupled thereto. One skilled in the art will understand that although IPG 104 is illustrated as being releasably coupled to anchoring device 102, IPG 104 and anchoring device 102 may alternatively be integrally formed.

Figure 6:
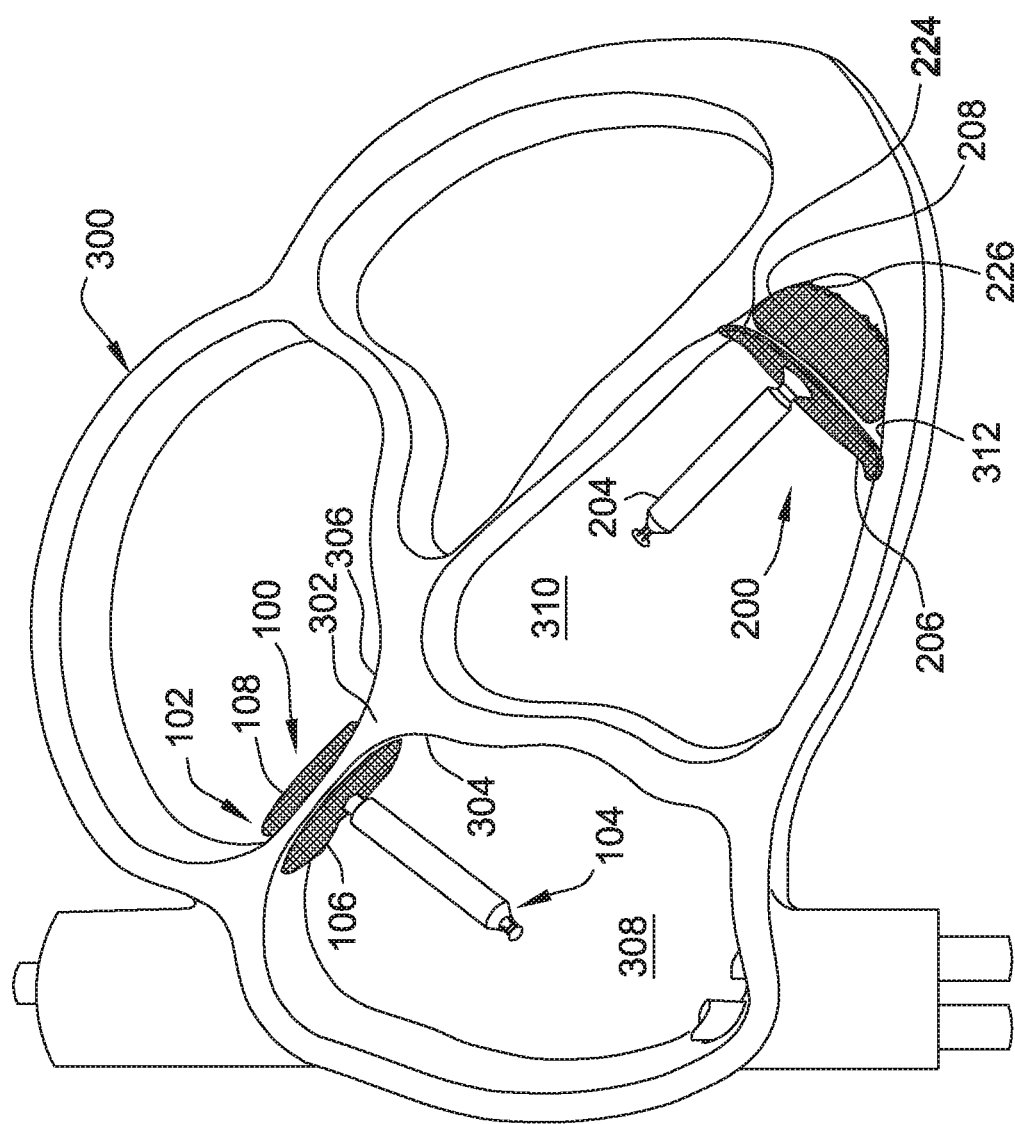
FIG. 6 shows the leadless pacemaker of FIG. 1 and the leadless pacemaker of FIG. 2 implanted into a heart.

Anchoring device 102 includes a proximal portion 106, a distal portion 108, and a reduced diameter portion 110 extending therebetween. In this particular embodiment, each of proximal portion 106 and distal portion 108 are disk-shaped, and, as illustrated in FIG. 6 and described in detail below, are sized and configured so as cover an opening or hole in a septal wall in which anchoring device 102 is positioned during delivery of leadless pacemaker 100. Although illustrated as substantially flat disks, it will be understood that proximal portion 106 and distal portion 108 may be configured as flat disks, concave disks, convex disks, or the like.

Proximal portion 106 and distal portion 108 may have any diameter suitable to overlie the opening or hole in the septum in which anchoring device 102 is to be deployed. Reduced diameter portion 110 has a diameter that is smaller than that of proximal portion 106 and distal portion 108. This reduced diameter allows proximal portion 106 and distal portion 108 to articulate with respect to one another for improved placement of anchoring device 102 within an opening or hole in the septal wall in which anchoring device 102 is to be deployed. Proximal portion 106 and distal portion 108 may have the same or different diameters ranging from 1 mm to 40 mm, including but not limited to 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 22 mm, 24 mm, 26 mm, 28 mm, 30 mm, 32 mm, 34 mm, 36 mm, 38 mm, and 40 mm.

Anchoring device 102 is formed of a tubular metal fabric formed of woven metal strands that are heat set during manufacturing into the desired configuration comprising proximal portion 106, distal portion 108, and reduced diameter portion 110. The woven metal strands are a plurality of conventional wire strands that have a predetermined relative orientation between the strands. The metal strands define two sets of essentially parallel generally helical stands, with the strands of one set having a "hand", i.e., a direction of rotation, opposite that of the other set. These helical strands define a generally tubular metal fabric, known in the metal fabric industry as a tubular braid.

The pitch of the wire strands (i.e., the angle defined between the turns of the wire and the axis of the braid) and the pick of the fabric (i.e., the number of wire crossovers per unit length) may be adjusted as known by those of skill in the art to increase/decrease/optimize the rigidity/strength as desired for a particular application. The wire strands of the metal fabric used to construct anchoring device 102 are desirably formed of a material that is both resilient and that can be heat treated to substantially set a desired shape. Materials that are suitable for this purpose include a cobalt-based low thermal expansion alloy referred to in the field as Elgeloy, nickel-based high temperature high-strength super-alloys commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by a molding process (described hereinbelow) when subjected to a predetermined heat treatment.

One class of materials that are desirable is memory-shape alloys. Such alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so.

One particularly desirable memory shape alloy for use in the present disclosure is nitinol, an approximately stoichiometric alloy of nickel and titanium, which may also include minor amounts of other metals to achieve desired properties. Nickel-titanium alloys are very elastic and are commonly referred to as "superelastic" or "pseudoelastic." The elasticity of these alloys helps a medical device return to an expanded configuration for deployment inside of the body following passage in a distorted or collapsed form through a delivery catheter. Nitinol is a particularly desirable alloy for forming the anchoring devices of the present disclosure.

The metal wires used to fabricate the anchoring devices of the present disclosure may include wires having a diameter of from about 0.002 to about 0.005 inches (about 0.051 to about 0.127 millimeters), desirably in the range of from about 0.003 to about 0.0035 inches (about 0.076 to about 0.089 millimeters), and in some embodiments, about 0.003 inches (about 0.076 millimeters). The number of wires in a wire mesh fabric (or tubular braid) may vary from about 36 to about 144, desirably from about 72 to about 144, and in some embodiments, 144. The pick count of the wire mesh may vary from about 30 to about 100, including from about 50 to about 80, including 70. As noted, the wire diameter and the number of wires in the wire mesh fabric will tend to influence the rigidity, strength, and flexibility of the anchoring device. Numerous other embodiments are contemplated within the scope of this disclosure. These combinations have been found to provide an appropriate combination of strength, rigidity, and flexibility for the anchoring device.

Anchoring device 102 further includes a securing mechanism 112 positioned on a distal side 114 of distal portion 108 and an IPG connector 116 (shown in FIG. 4 and discussed in more detail below) positioned on a proximal side 118 of proximal portion 106. Each of securing mechanism 112 and IPG connector 116 are configured to secure or retain the distal ends and the proximal ends, respectively, of the tubular metal fabric used to form anchoring device 102 so as to prevent fraying or unraveling of the ends. In one embodiment, securing mechanism 112 and/or IPG connector 116 are formed of or include a radiopaque marker material for use in the delivery and deployment of anchoring device 102 at a target site. Further, an electrical connection 120 (shown in FIG. 5 and discussed in more detail below) comprising at least one pacing electrode or contact point (not shown in FIG. 1) extends from IPG connector 116 (or IPG 104 itself when IPG 104 and anchoring device 102 are integrally formed) to at least a portion of an outer surface of proximal portion 106 such that the at least one pacing electrode is configured to contact tissue at the target site.

Referring now to FIG. 2, there is shown another embodiment of a leadless pacemaker 200 according to the present disclosure. Similar to leadless pacemaker 100, leadless pacemaker 200 includes an anchoring device 202 and an IPG 204 coupled thereto. One skilled in the art will understand that although IPG 204 is illustrated as being releasably coupled to anchoring device 202, IPG 204 and anchoring device 202 may alternatively be integrally formed.

Anchoring device 202 includes a proximal portion 206, a distal portion 208, and a reduced diameter portion 210 extending therebetween. In this particular embodiment, proximal portion 206 is disk-shaped and distal portion 208 is cylindrically-shaped, and, as illustrated in FIG. 6 and described in detail below, are sized and configured so as to contact tissue within a target site, and in particular a right or left ventricle of a heart, in which anchoring device 202 is positioned during delivery and deployment of pacemaker 200. Although illustrated as a substantially flat disk, it will be understood that proximal portion 206 may be configured as a flat disk, concave disk, convex disk, or the like. Further, although illustrated as substantially cylindrically-shaped, it will be understood that distal portion 208 may be cone-shaped, bulbous, strawberry-shaped, mushroom-shaped, elliptical or the like so long as distal portion 208 is capable of contacting and being anchored to tissue at the target site as described in more detail below.

Proximal portion 206 may have any diameter suitable to enable contact between tissue at the target site and pacing electrodes 222 (not shown in FIG. 2; discussed in more detail below) on a distal side 224 of proximal portion 206. Further, distal portion 208 may have any depth, thickness, and diameter suitable to enable contact between tissue at the target site and an outer surface of distal portion 208 to allow for anchoring, fixing, attaching, and/or positioning distal portion 208 at the target site. Proximal portion 206 and distal portion 208 may have the same or different diameters ranging from 1 mm to 40 mm, including but not limited to 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 22 mm, 24 mm, 26 mm, 28 mm, 30 mm, 32 mm, 34 mm, 36 mm, 38 mm, and 40 mm. In the embodiment illustrated in FIG. 2, proximal portion 206 has a larger diameter than distal portion 208.

In one embodiment, distal portion 208 includes hooks 226 coupled thereto and configured so as to anchor, affix, attach, and/or position distal portion 208 to tissue at the target site with reduced or minimal trauma to the tissue. Further, reduced diameter portion 210 has a diameter that is smaller than that of proximal portion 206 and distal portion 208. This reduced diameter allows proximal portion 206 and distal portion 208 to articulate with respect to one another for improved placement of anchoring device 202 within a target site, such as within a right or left ventricle, in which anchoring device 202 is to be deployed.

Similar to anchoring device 102, anchoring device 202 is formed of a tubular metal fabric formed of woven metal strands that are heat set during manufacturing into the desired configuration comprising proximal portion 206, distal portion 208, and reduced diameter portion 210.

Anchoring device 202 further includes a securing mechanism 212 positioned on a distal side 214 of distal portion 208 and an IPG connector 216 (shown in FIG. 4 and discussed in more detail below with respect to leadless pacemaker 100) positioned on a proximal side 218 of proximal portion 206. Each of securing mechanism 212 and IPG connector 216 are configured to secure or retain the distal ends and the proximal ends, respectively, of the tubular metal fabric used to form anchoring device 202 so as to prevent fraying or unraveling of the ends. In one embodiment, securing mechanism 212 and/or IPG connector 216 are formed of or include a radiopaque marker material for use in the delivery and deployment of anchoring device 202 at a target site.

Further, an electrical connection 220 (discussed in more detail below with respect to leadless pacemaker 100) comprising at least one pacing electrode or contact point (not shown in FIG. 2) extends from IPG connector 216 (or IPG 204 itself wherein IPG 204 and anchoring device 202 are integrally formed) to at least a portion of an outer surface of proximal portion 206 such that the at least one pacing electrode is configured to contact tissue at the target site. In an alternative embodiment, electrical connection 220 may be configured such that it extends from IPG connector 216 to at least a portion of an outer surface of distal portion 208 (in addition to or in lieu of an outer surface of proximal portion 206) such that the at least one pacing electrode is configured to contact tissue at the target site.

In FIG. 3, there is shown another embodiment of a leadless pacemaker 500 according to the present disclosure. Similar to leadless pacemaker 200, leadless pacemaker 500 includes an anchoring device 502 and an IPG 504 coupled thereto. One skilled in the art will understand that although IPG 504 is illustrated as being releasably coupled to anchoring device 502, IPG 504 and anchoring device 502 may alternatively be integrally formed.

Similar to anchoring device 202, anchoring device 502 is formed of a tubular metal fabric formed of woven metal strands that are heat set during manufacturing into the desired configuration. In contrast to anchoring device 202, however, anchoring device 502 includes only one expanded portion 506. In this particular embodiment, expanded portion 506 is cylindrically-shaped, and, as illustrated below in FIG. 7 and described in detail below, is sized and configured so as to contact, or frictionally engage, tissue within a target site, and in particular in a right or left ventricle of a heart, in which anchoring device 502 is positioned during delivery of pacemaker 500. Although illustrated as substantially cylindrically-shaped, it will be understood that expanded portion 506 may be cone-shaped, bulbous, strawberry-shaped, mushroom-shaped, elliptical, or the like so long as expanded portion 506 is capable of contacting and frictionally engaging tissue at the target site as described in more detail below.

Expanded portion 506 may have any size and configuration suitable to enable contact, or frictional engagement, between tissue at the target site and an outer surface thereof, to allow for anchoring, fixing, attaching, and/or positioning expanded portion 506 at the target site, and to enable contact between tissue at the target site and pacing electrodes 522 (not shown in FIG. 3; discussed in more detail below). For example, expanded portion 506 may have a diameter ranging from 1 mm to 40 mm, including but not limited to 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 22 mm, 24 mm, 26 mm, 28 mm, 30 mm, 32 mm, 34 mm, 36 mm, 38 mm, and 40 mm. In one embodiment, expanded portion 506 includes hooks 526 coupled thereto and configured so as to anchor, affix, attach, and/or position expanded portion 506 to tissue at the target site with reduced or minimal trauma to the tissue.

Anchoring device 502 further includes a securing mechanism 512 positioned on a distal side 514 of expanded portion 506 and an IPG connector 516 (shown in FIG. 4 and discussed in more detail below with respect to leadless pacemaker 100) positioned on a proximal side 518 of expanded portion 506. Each of securing mechanism 512 and IPG connector 516 are configured to secure or retain the distal ends and the proximal ends, respectively, of the tubular metal fabric used to form anchoring device 502 so as to prevent fraying or unraveling of the ends. In one embodiment, securing mechanism 512 and/or IPG connector 516 are formed of or include a radiopaque marker material for use in the delivery and deployment of anchoring device 502 at a target site. Further, an electrical connection 520 (discussed in more detail below with respect to leadless pacemaker 100) comprising at least one pacing electrode or contact point (not shown in FIG. 3) extends from IPG connector 516 (or IPG 504 itself when IPG 504 and anchoring device 502 are integrally formed) to at least a portion of an outer surface of expanded portion 506 such that the at least one pacing electrode is configured to contact tissue at the target site.

Figure 4:
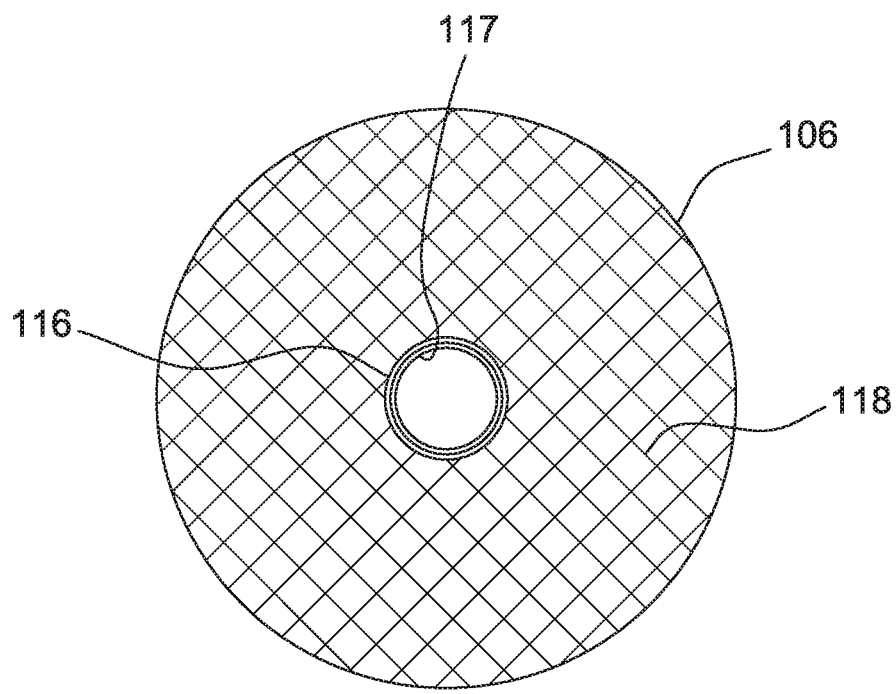
FIG. 4 shows a proximal end view of the collapsible anchoring device of FIG. 1.
Figure 5:
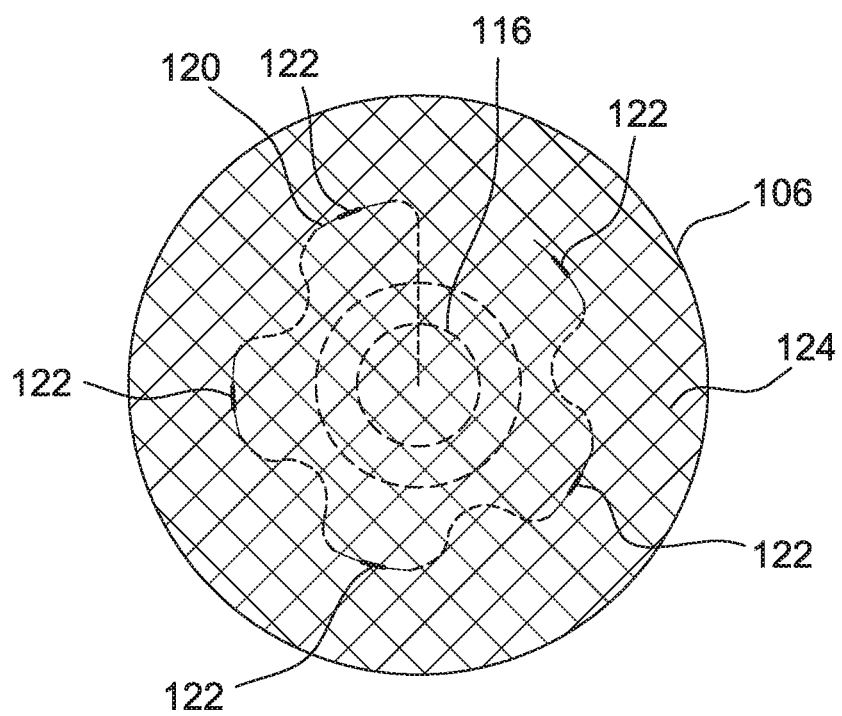
FIG. 5 shows a distal end view of a portion of the collapsible anchoring device of FIG. 1.

FIG. 4 illustrates a proximal end view of proximal portion 106 illustrated in FIG. 1, and FIG. 5 illustrates a distal end view of proximal portion 106 illustrated in FIG. 1. It should be understood that although FIGS. 4 and 5 reference IPG connector 116 and electrical connection 120 positioned on proximal portion 106 of anchoring device 102 as depicted in FIG. 1, the disclosure below is equally applicable to IPG connector 216 and electrical connection 220 positioned on proximal portion 206 of anchoring device 202 as depicted in FIG. 2 and to IPG connector 516 and electrical connection 520 positioned on expanded portion 506 as depicted in FIG. 3.

As illustrated in FIG. 4, IPG connector 116 is positioned substantially at the center of proximal side 118 of proximal portion 106. IPG connector 116 comprises a threaded opening 117 configured to engage threads on a distal end of IPG 104 (not shown) such that IPG 104 may be removable from IPG connector 116, and thus from anchoring device 102. In addition, IPG connector 116 is also configured such that it may engage a delivery device, such as a delivery catheter, during delivery and deployment of anchoring device 102. Although IPG connector 116 is illustrated in FIG. 4 as providing for a threaded engagement with either IPG 104 or a delivery device, it will be understood by one skilled in the art that IPG connector 116 may include any suitable means for releasably coupling IPG connector 116 to IPG 104 or to a delivery device. Suitable means for releasable coupling include, for example but not limited to, twist locks, snap fit couplings, magnetic couplings, ball detent/quick connects, ball lock couplings or connections, and the like. Further, it will be understood by one skilled in the art that although proximal portion 106 is illustrated as being releasably coupled to IPG 104 via IPG connector 116, proximal portion 106, and thus anchoring device 102, may alternatively be integrally formed with IPG 104.

As illustrated in FIG. 5, electrical connection 120 extends from IPG connector 116 and around at least a portion of a circumference of proximal portion 106. Although electrical connection 120 is illustrated as extending around at least portion of a circumference of proximal portion 106, it will be understood by one skilled in the art that electrical connection 120 may extend along any path such that electrical connection 120 is configured to provide contact between at least one pacing electrode 122 and tissue at the target site so as to provide the desired pacing. In one embodiment, electrical connection 120 is an insulated, electrically conductive wire configured to receive power from an external power source, such as IPG 104 or a delivery device (neither shown in FIG. 5). Suitable electrically conductive wires include platinum, and suitable insulating materials include silicone or any other material suitable for hermetically insulating the conductive wire.

Electrical connection 120 includes pacing electrodes 122 (also referred to herein as contact points) positioned about an outer surface of proximal portion 106. Although electrical connection 120 is illustrated in FIG. 4 as including five pacing electrodes 122, it will be understood by one skilled in the art that electrical connection 120 may comprise any number of pacing electrodes including but not limited to, one, two, three, four, five, six, seven or more pacing electrodes 122. In one embodiment, pacing electrodes 122 are formed by removing a portion of the insulating material from electrical connection 120 such that a portion of the electrically conductive wire of electrical connection 120 is exposed and may contact tissue at a target site. In another embodiment, pacing electrodes 122 are ring electrodes electrically coupled to electrical connection 120. It will be understood by one skilled in the art that pacing electrodes 122 may be any type of electrode suitable to receive power or energy from an external source and to transmit that power or energy to tissue at the target site. Pacing electrodes 122 may be individually selected to receive power or energy such that any combination of pacing electrodes 122 (i.e., a single pacing electrode 122, a combination of two or more pacing electrodes 122, or all pacing electrodes 122) may be energized at any point.

As shown in FIG. 5, electrical connection 120 may be secured to proximal portion 106 by weaving electrical connection 120 within the wire strands of distal side 124 of proximal portion 106 such that pacing electrodes 122 are positioned on an outer surface of distal side 124 of proximal portion 106. In one embodiment, electrical connection 120 is secured to proximal portion 106 with threads, sutures or the like (not shown) or may be molded or braided into proximal portion 106 with or without the use of threads, sutures, or the like.

FIG. 6 illustrates leadless pacemaker 100 and leadless pacemaker 200 deployed within a heart 300. Leadless pacemaker 100 is positioned within atrial septal wall 302 such that anchoring device 102 extends through atrial septal wall 302 with proximal portion 106, including electrical connection 120 and pacing electrodes 122 (not shown in FIG. 5), positioned on the right atrial wall 304, distal portion 108 positioned on the left atrial wall 306, and reduced diameter portion 110 (not shown in FIG. 5) extending through atrial septal wall 302. IPG 104 is coupled to proximal portion 106 via IPG connector 116 (not shown in FIG. 5) and extends into the right atrium 308.

Leadless pacemaker 200 is positioned within right ventricle 310 such that hooks 226 on distal portion 208 engage right ventricular wall 312 and distal side 224 of proximal portion 206, including electrical connection 220 and pacing electrodes 222 (not shown in FIG. 5), is in contact with right ventricular wall 312. IPG 204 is coupled to proximal portion 206 via IPG connector 216 (not shown in FIG. 5) and extends into right ventricle 310.

Figure 7:
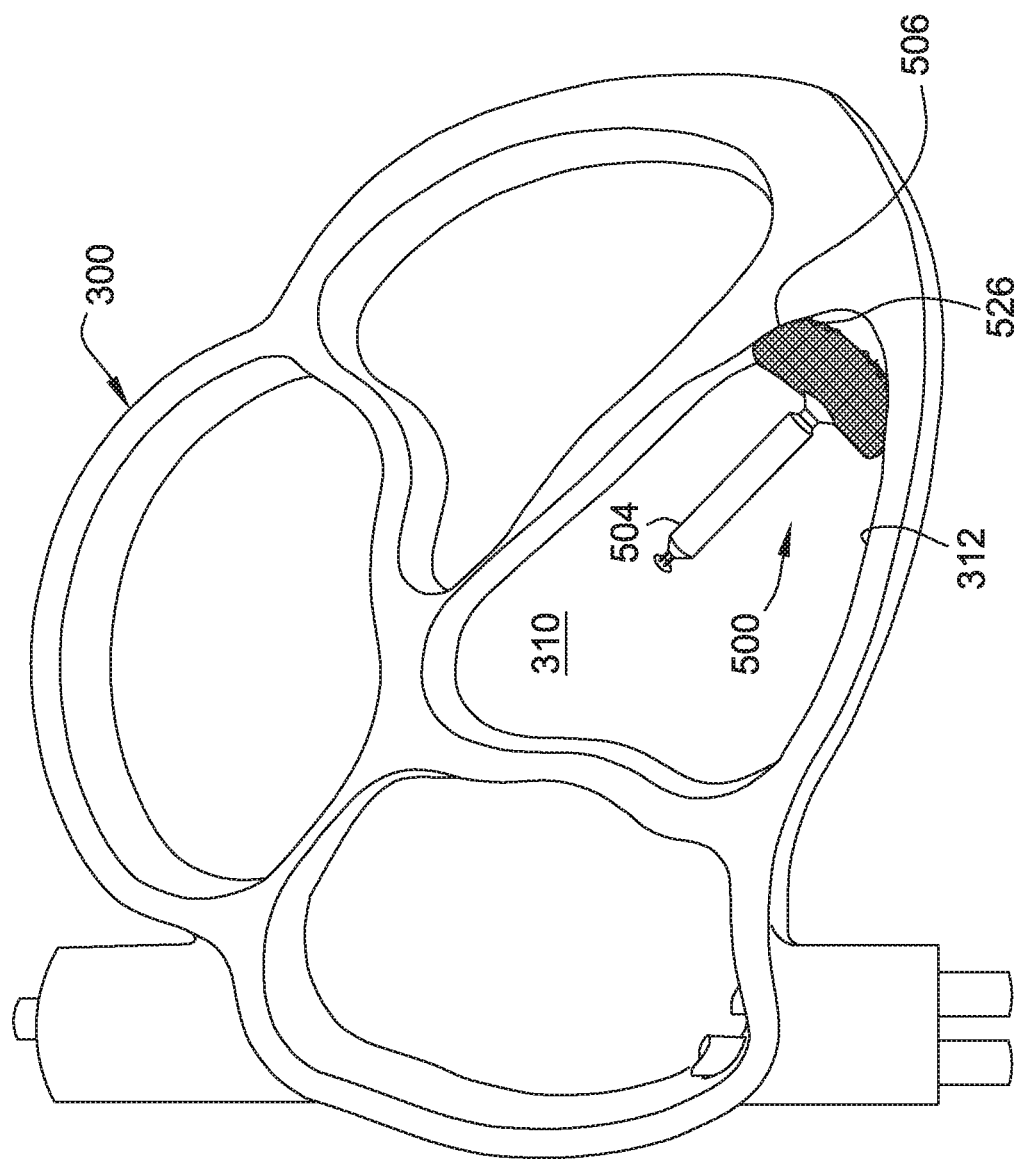
FIG. 7 shows the leadless pacemaker of FIG. 3 implanted into a heart.

FIG. 7 illustrates leadless pacemaker 500 deployed within a heart 300. Leadless pacemaker 500 is positioned within right ventricle 310 such that hooks 526 on expanded portion 506 engage right ventricular wall 312 and pacing electrodes 522 (not shown in FIG. 7), are in contact with right ventricular wall 312. IPG 504 is coupled to expanded portion 506 via IPG connector 516 (not shown in FIG. 7) and extends into right ventricle 310.

Figure 8A:
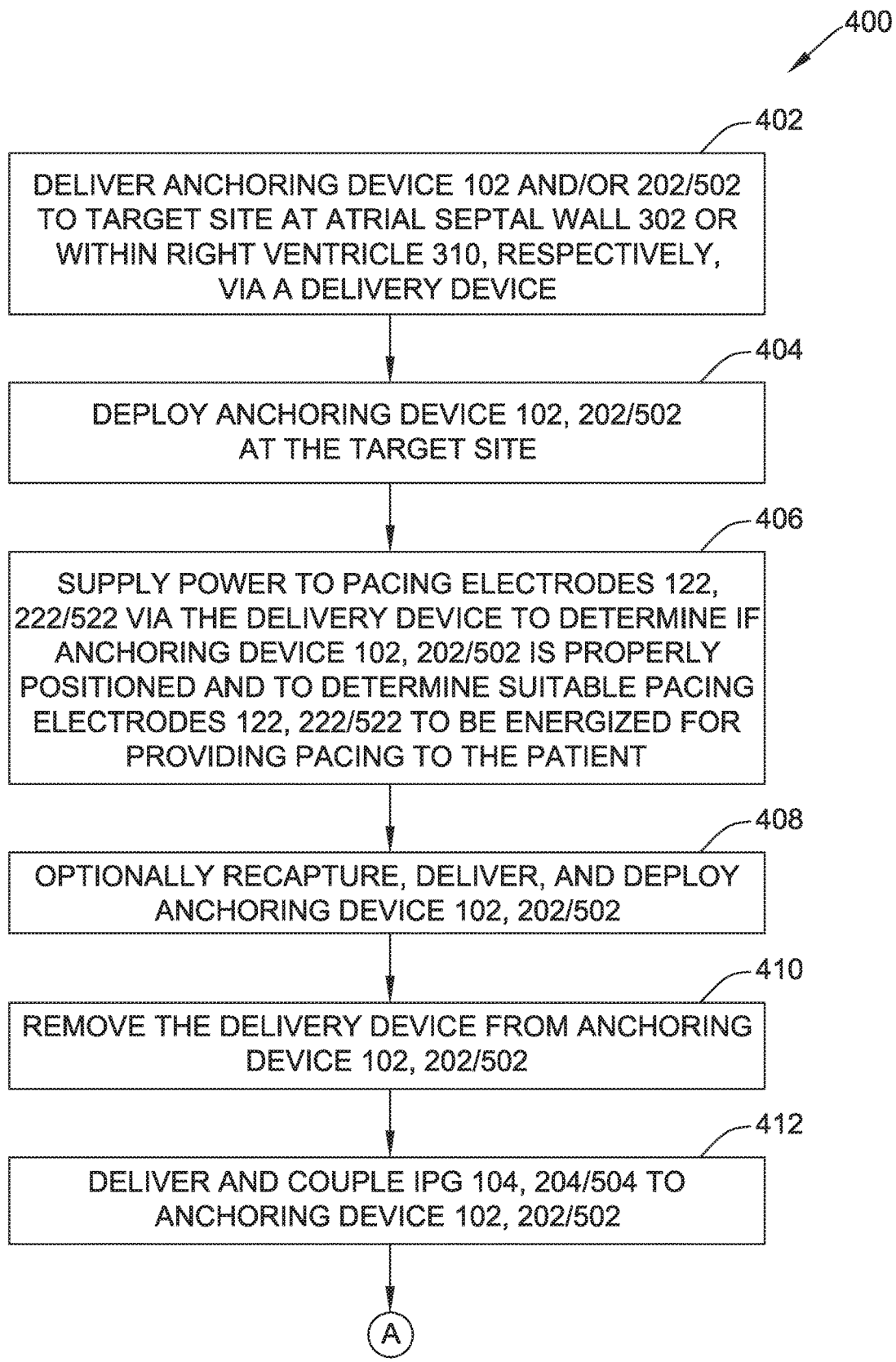
FIG. 8 is a flow chart of one embodiment of a method of delivering a leadless pacemaker according to the present disclosure.
Figure 8B:
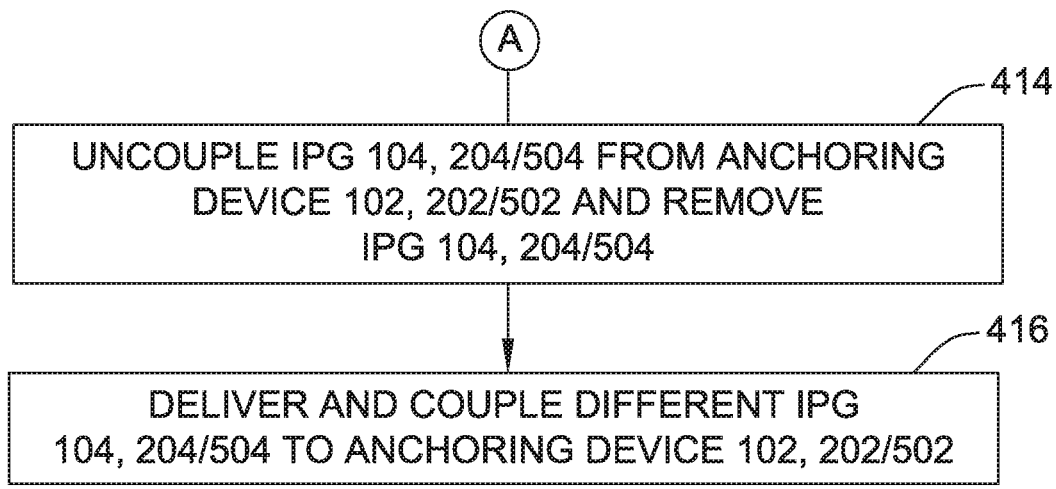

FIG. 8 is a flow chart illustrating an exemplary method 400 of delivering leadless pacemakers 100, 200, 500 to heart 300. Method 400 includes delivering 402 anchoring device 102 and/or anchoring device 202/502 to a target site at atrial septal wall 302 or within right ventricle 310, respectively, via a delivery device, such as a delivery catheter, and deploying 404 anchoring devices 102, 202/502 at the target site, as is known in the art (as described in, for example, U.S. Pub. No. 2009/0171386 incorporated herein by reference). One skilled in the art will appreciate that leadless pacemaker 100 and leadless pacemaker 200/500 may be utilized separately for single chamber pacing or in combination for dual-chamber pacing. One skilled in the art will further appreciate that leadless pacemaker 100, 200/500, although illustrated as being delivered such that pacing is provided to the right atrium and the right ventricle, respectively, may be delivered such that pacing is provided to the left atrium and/or the left ventricle.

Once anchoring device 102, 202/502 is initially delivered and deployed within the target site, power is supplied 406 to pacing electrodes 122, 222/522 via the delivery device to determine if anchoring device 102, 202/502 is properly positioned and to determine suitable pacing electrodes 122, 222/522 to be energized for providing pacing to the patient. It will be understood by one skilled in the art that power may be supplied to pacing electrodes 122, 222/522 via IPG 104, 204/504 as opposed to the delivery device if desired. If it is determined that anchoring device 102, 202/502 should be repositioned within heart 300, anchoring device 102, 202/502 may optionally be recaptured 408 within the delivery device and repositioned and redeployed accordingly. Once proper positioning of anchoring device 102, 202/502 is determined, the delivery device is removed 410 from anchoring device 102, 202/502, and IPG 104, 204/504 is delivered and coupled 412 to anchoring device 102, 202, respectively. It will be appreciated that the same delivery device utilized for delivering and deploying anchoring device 102, 202/502 or a different delivery device may be used to deliver and couple IPG 104, 204/504.

If at any point it is determined that IPG 104, 204/504 is defective or inoperative, the battery life of IPG 104, 204/504 has expired (i.e., IPG 104, 204 is "dead"), or retrieval of IPG 104, 204/504 is desired for any other reason, IPG 104, 204/504 can be uncoupled 414 from anchoring device 102, 202/502 and removed. If it is determined that further pacing is still desired, a different IPG may then be delivered and coupled 416 to anchoring device 102, 202/502 to provide the further pacing. If it is desired that pacing is no longer desired or necessary, IPG 104, 204/504 may be removed while anchoring device 102, 202/502 remains within heart 300. Because anchoring device 102, 202/502 is constructed from an expandable, tubular, metal braided fabric, similar to many heart occluders known in the art, it is not necessary to remove anchoring device 102, 202/502 from heart 300 as it may be conformed to and fully engrossed in tissue at the target site thus closing any hole present between the atria and preventing or minimizing any tissue damage that could occur during removal of anchoring device 102, 202/502.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A leadless pacemaker comprising:
    an implantable pulse generator; and
    a collapsible anchoring device configured to be coupled to the implantable pulse generator, the collapsible anchoring device comprising:
        at least one pacing electrode configured to contact tissue at a target site;
        an implantable pulse generator connector on a proximal side of the collapsible anchoring device, wherein the implantable pulse generator connector comprises a threaded connector configured to releasably engage threads disposed on a distal end of the implantable pulse generator such that the implantable pulse generator extends from the proximal side of the collapsible anchoring device in a proximal direction; and
        an electrical connection extending from the implantable pulse generator connector to the collapsible anchoring device, wherein the at least one pacing electrode is disposed on the electrical connection.

2. The leadless pacemaker of claim 1, wherein the collapsible anchoring device is formed from a tubular member having a proximal end and a distal end, the tubular member having an expanded configuration and configured to be constrained to a reduced configuration for delivery to a target site.

3. The leadless pacemaker of claim 2, wherein the tubular member comprises a braided fabric material, and wherein the braided fabric material comprises a metal alloy selected from the group consisting of stainless steel, nickel-titanium, and cobalt-chromium-nickel.

4. The leadless pacemaker of claim 1, wherein the collapsible anchoring device comprises:
    a proximal portion; and
    a distal portion coupled to the proximal portion via a reduced diameter portion,
    wherein the at least one pacing electrode is positioned on a distal side of the proximal portion, wherein the proximal portion is disk-shaped, and wherein the distal portion is disk-shaped.

5. The leadless pacemaker of claim 4, wherein the reduced diameter portion is configured for placement through an opening in a septal wall, the proximal portion is configured for placement adjacent a proximal side of the septal wall, and the distal portion is configured for placement adjacent a distal side of the septal wall.

6. The leadless pacemaker of claim 4, wherein the distal portion is cylindrically-shaped, and wherein the distal portion further comprises:
a plurality of hooks extending from an outer surface of the distal portion and configured to engage the tissue at the target site.

7. The leadless pacemaker of claim 6, wherein the collapsible anchoring device is configured to frictionally engage the tissue at the target site.

8. The leadless pacemaker of claim 1, wherein the collapsible anchoring device is configured to frictionally engage the tissue at the target site, wherein the collapsible anchoring device is formed from a tubular member having an expanded configuration, and wherein the tubular member in the expanded configuration is one of cylindrically-shaped, cone-shaped, strawberry-shaped, or bulbous.

9. The leadless pacemaker of claim 8 further comprising:
a plurality of hooks extending from an outer surface of the tubular member and configured to engage the tissue at the target site.

10. An anchoring device for a leadless pacemaker, the anchoring device comprising:
a tubular member having a proximal end, a distal end, and an expanded configuration, the tubular member comprising an implantable pulse generator connector positioned on a proximal side thereof, the implantable pulse generator connector comprising a threaded connector configured to engage threads positioned on a distal end of an implantable pulse generator to couple the implantable pulse generator to the proximal side of the tubular member such that the implantable pulse generator extends away from the anchoring device in a proximal direction; and
an electrical connection comprising at least one pacing electrode, wherein the electrical connection extends from the implantable pulse generator connector to an outer surface of the tubular member such that at least one pacing electrode is configured to contact tissue at a target site, and wherein the electrical connection comprises an electrically conductive, insulated wire comprising at least one non-insulated portion forming the at least one pacing electrode.

11. The anchoring device of claim 10, wherein the tubular member is configured to be constrained to a reduced configuration for delivery to a target site, wherein the tubular member comprises a braided fabric material, and wherein the braided fabric material comprises a metal alloy selected from the group consisting of stainless steel, nickel-titanium, and cobalt-chromium-nickel.

12. The anchoring device of claim 10, wherein the tubular member comprises:
a proximal portion, wherein the implantable pulse generator connector is positioned on a proximal side of the proximal portion; and
a distal portion coupled to the proximal portion via a reduced diameter portion,
wherein the at least one pacing electrode is positioned on a distal side of the proximal portion, wherein the proximal portion is disk-shaped, and wherein the distal portion is disk-shaped.

13. The anchoring device of claim 12, wherein the reduced diameter portion is configured for placement through an opening in a septal wall, the proximal portion is configured for placement adjacent a proximal side of the septal wall, and the distal portion is configured for placement adjacent a distal side of the septal wall.

14. The anchoring device of claim 12, wherein the distal portion is cylindrically-shaped, and wherein the tubular member is configured to frictionally engage the tissue at the target site.

15. The anchoring device of claim 14, wherein the distal portion further comprises a plurality of hooks extending from an outer surface of the distal portion and configured to engage the tissue at the target site.

16. The anchoring device of claim 10, wherein the tubular member is configured to frictionally engage the tissue at the target site, wherein the tubular member has an expanded configuration that is one of cylindrically-shaped, cone-shaped, strawberry-shaped, or bulbous.

17. The anchoring device of claim 16 further comprising:
a plurality of hooks extending from an outer surface of the tubular member and configured to engage the tissue at the target site.

18. A method of delivering a leadless pacemaker to a target site, the method comprising:
providing an anchoring device comprising a tubular member having a proximal end, a distal end and an expanded configuration, the tubular member comprising an implantable pulse generator connector positioned on a proximal side thereof and an electrical connection extending from the implantable pulse generator to an outer surface of the tubular member such that the at least one pacing electrode is configured to contact tissue at a target site, wherein the implantable pulse generator connector includes a threaded connector configured to engage threads positioned on a distal end of an implantable pulse generator, and wherein the electrical connection comprises an electrically conductive, insulated wire comprising at least one non-insulated portion forming the at least one pacing electrode;
advancing the anchoring device in a reduced configuration to the target site through a delivery device;
deploying the anchoring device from the delivery device such that the anchoring device at least partially returns from the reduced configuration to an expanded configuration; and
coupling the implantable pulse generator to the anchoring device via the implantable pulse generator connector.

* * * * *